US00PP09713P

United States Patent [19]

Polys

[11] Patent Number: Plant 9,713

[45] Date of Patent: Nov. 26, 1996

[54] CHRYSANTHEMUM PLANT NAMED 'YELLOW CHERIE'

[75] Inventor: Susan M. Polys, Salinas, Calif.

[73] Assignee: Yoder Brothers, Inc., Barberton, Ohio

[21] Appl. No.: 523,290

[22] Filed: Sep. 5, 1995

[51] Int. Cl.[6] ..... A01H 5/00

[52] U.S. Cl. ..... Plt./82.2

[58] Field of Search ..... Plt./82.2

[56] References Cited

U.S. PATENT DOCUMENTS

| | | | |
|---|---|---|---|
| P.P. 8,695 | 4/1994 | Polys | Plt./82.2 |
| P.P. 8,807 | 6/1994 | Polys | Plt./82.2 |
| 4,616,099 | 10/1986 | Sparkes | 47/58 |

OTHER PUBLICATIONS

Broertjes, et al., 1980, "A mutant of a mutant of a . . . Irradiation of progressive radiation–induced mutants in a mutation breeding programme with *Chrysanthemum morifolium", Euphytica, 9: 525–530.*

Gosling, ed., 1979, "the Chrysanthemum Manual–6th edition", the National Chrysanthemum Society London, Essex Telegraph press, Ltd., pp. 329–336.

Broertjes, et al., 1978, "Application of Mutation Breeding Methods in the Improvement of Vegetatively Propagatede Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by X–rays", Am. Soc. Hort. Sci. Proc., pp. 613 . 620.

Broertjes, 1966, "Mutation breeding of chrysanthemums", Euphytica, 15:156–162.

Dowrick, et al., 1966, "The induction of mutations in Chrysanthemum using X–and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Yellow Cherie particularly characterized by its flat capitulum flat capitulum form; daisy capitulum type; yellow ray floret color; diameter across face of capitulum of 35 to 44 mm when fully opened, when grown as a pinched spray pot mum; very floriferous, with excellent display of many small flowers; photoperiodic flowering response of 50 to 53 days after start of short days; plant height, with 13 to 14 long days after sticking unrooted cuttings and with 0 to 1 applications of 2500 ppm B-9 SP ranges from 20 to 25 cm when grown as a pinched pot mum with 4 cuttings in a 15 cm pot; branching pattern is spreading and prolific, each plant having 7 to 9 laterals after pinch; and recommended as a spray pot mum.

1 Drawing Sheet

The present invention comprises a new and distinct cultivar of Chrysanthemum, botanically known as *Dendranthema grandiflora,* and referred to by the cultivar name Yellow Cherie.

Yellow Cherie, identified as 5491 (89-114H03), is a product of a mutation induction program. The new cultivar was discovered and selected by inventor Susan M. Polys on May 21, 1993 in a controlled environment in Salinas, Calif. as one flowering plant within a flowering block established as rooted cuttings from stock plants which had been exposed as unrooted cuttings to an X-ray source of 1500 rads in Fort Myers, Fla. on Dec. 3, 1992. The irradiated parent cultivar was the cultivar Honey Cherie, disclosed in U.S. Plant Pat. No. 8,695 and described as a flat daisy spray pot mum with soft honey-bronze ray floret color.

The irradiation program resulting in Yellow Cherie had as its primary objective the expansion of color ranges of the parent cultivar Honey Cherie. The irradiation program comprised irradiation of cuttings of the parent cultivar at irradiation levels of 1500, 1750 and 2000 rads. A total of 1522 cuttings harvested from a total of 225 irradiated plants were planted on Mar. 8, 1993. Of these, 9 initial selections were made, which selections were then revegetated and reflowered. Three consecutive flowerings resulted in discarding 6 of the original 9 selections on Jan. 24, 1994. The remaining three selections were maintained as PIs (Possible Introductions) and further trialed in Salinas, Calif. and Leamington, Ontario, Canada, ultimately resulting in the decision to introduce one selection as Yellow Cherie and one selection as Bronze Cherie. The one remaining selection is still being trailed. Bronze Cherie is disclosed in pending application Ser. No. 08/523,288 of applicant.

The first act of asexual reproduction of Yellow Cherie was accomplished when vegetative cuttings were taken from the initial selection in July of 1993 in a controlled environment in Salinas, Calif., by technicians working under supervision of Susan M. Polys.

Horticultural examination of controlled flowerings of successive plantings has shown that the unique combination of characteristics as herein disclosed for Yellow Cherie are firmly fixed and are retained through successive generations of asexual reproduction.

Yellow Cherie has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Leamington, Ontario, Canada, under greenhouse conditions which approximate those generally used in commercial greenhouse practice.

The following traits have been repeatedly observed and are determined to be basic characteristics of Yellow Cherie, which, in combination, distinguish this Chrysanthemum as a new and distinct cultivar:

1. Flat capitulum form.
2. Daisy capitulum type.
3. Yellow ray floret color.
4. Diameter across face of capitulum of 35 to 44 mm when fully opened, when grown as a pinched spray pot mum.
5. Very floriferous, with excellent display of many small flowers.

6. Photoperiodic flowering response of 50 to 53 days after start of short days.

7. Plant height, with 13 to 14 long days after sticking unrooted cuttings and with 0 to 1 applications of 2500 ppm B-9 SP ranges from 20 to 25 cm when grown as a pinched pot mum with 4 cuttings in a 15 cm pot.

8. Branching pattern is spreading and prolific, each plant having 7 to 9 laterals after pinch.

9. Recommended as a spray pot mum.

The accompanying photographic drawing is a side view of Yellow Cherie, grown as a spray pot mum with 4 cuttings in a 15 cm pot, with the colors being as nearly true as possible with illustrating of this type.

Of the commercial cultivars known to the inventor, the most similar in comparison to Yellow Cherie is the parent cultivar Honey Cherie. All traits of Yellow Cherie are similar to those of Honey Cherie, except for the ray floret color. The ray floret color of Yellow Cherie is clear yellow (RHS 3A to 3B), while the ray floret color of Honey Cherie is described as soft honey-bronze (RHS 12B, overlaid and slightly streaked with 163B).

In the following description color references are made to The Royal Horticultural Society Colour Chart. The color values were determined on plant material grown as a pinched pot mum with 4 cuttings in a 15 cm pot in Salinas, Calif. on May 17, 1995.

Classification:

*Botanical.*—*Dendranthema grandiflora* cv Yellow Cherie.

*Commercial.*—Flat daisy spray pot mum.

INFLORESCENCE

A. Capitulum:

*Form.*—Flat

*Type.*—Daisy.

*Diameter across face.*—35 to 44 mm when fully opened.

B. Corolla of ray florets:

*Color (general tonality from a distance of three meters).*—Yellow.

*Color (upper surface).*—3A to 3B.

*Color (under surface).*—3C.

*Shape.*—Straight, oblong, slightly ribbed.

C. Corolla of disc florets:

*Color (mature).*—14A.

*Color (immature).*14B, center overlaid with 144B.

D. Reproductive organs:

*Androecium.*—Present on disc florets only; moderate pollen.

*Gynoecium.*—Present on both ray and disc florets.

PLANT

A. General appearance:

*Height.*—20 to 25 cm when grown as a pinched pot mum with 13 to 14 long days after sticking unrooted cuttings prior to start of short days and with 0 to 1 applications of 2500 ppm B-9 SP.

*Branching pattern.*—Spreading and prolific, with 7 to 9 laterals after pinch.

B. Foliage:

*Color (upper surface).*—147A.

*Color (under surface).*—147B.

*Shape.*—Small, lobed, slightly serrated.

What is claimed is:

1. A new and distinct Chrysanthemum plant named Yellow Cherie, as described and illustrated.

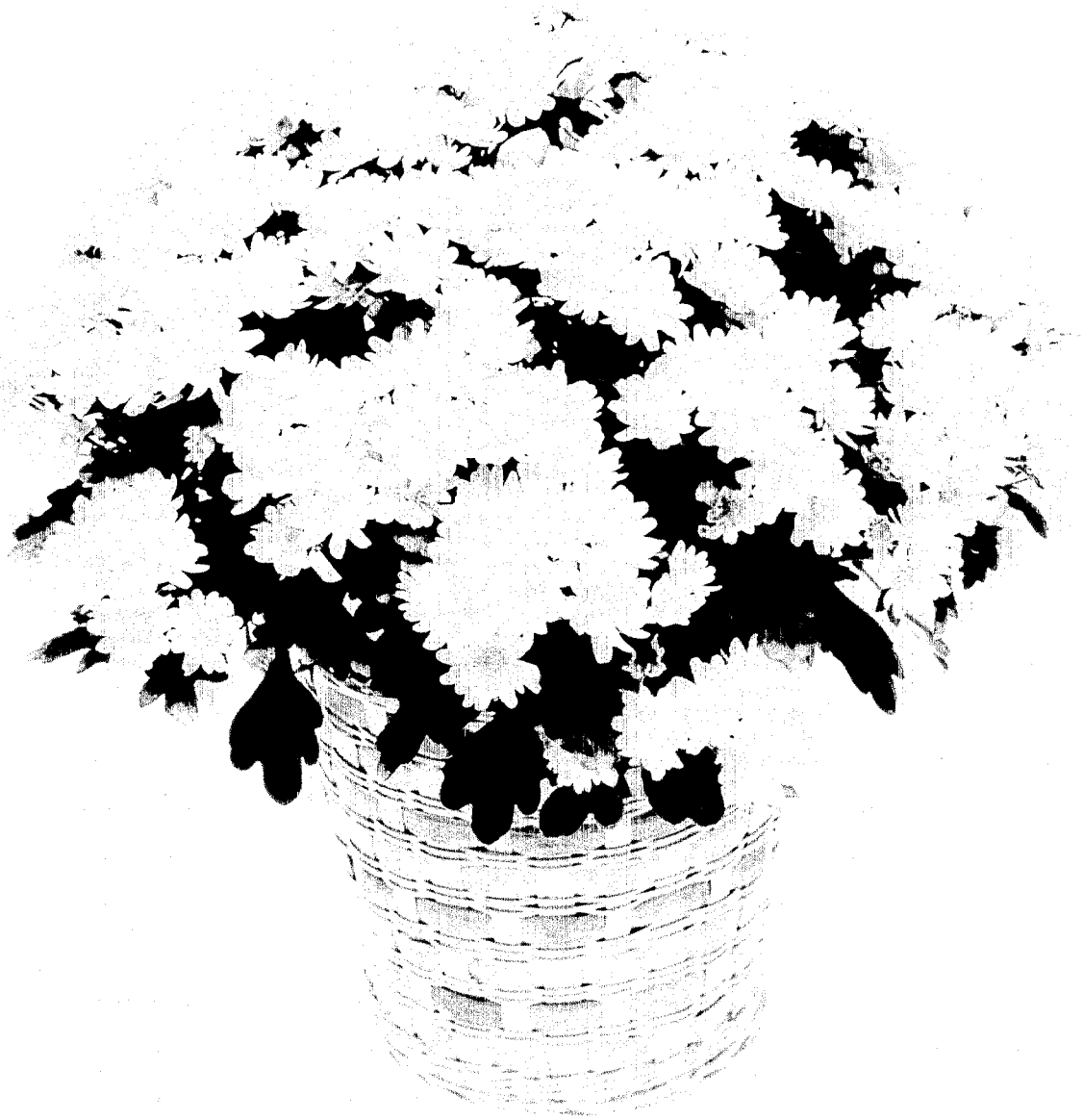

* * * * *